United States Patent
Wilczek et al.

(10) Patent No.: US 7,268,246 B2
(45) Date of Patent: Sep. 11, 2007

(54) PREPARATION AND USE OF REACTIVE ORGANOSILICON COMPOUNDS

(75) Inventors: Lech Wilczek, Wilmington, DE (US); Isao Nagata, Sakura (JP)

(73) Assignee: E.I. du Pont de Nemours and Company, Wilmington, DE (US)

( * ) Notice: Subject to any disclaimer, the term of this patent is extended or adjusted under 35 U.S.C. 154(b) by 34 days.

(21) Appl. No.: 11/012,843

(22) Filed: Dec. 15, 2004

(65) Prior Publication Data

US 2006/0128920 A1 Jun. 15, 2006

(51) Int. Cl.
   *C07F 7/18* (2006.01)
(52) U.S. Cl. .................. 556/437; 525/100; 525/431; 525/446; 525/464; 528/26
(58) Field of Classification Search ............ None
   See application file for complete search history.

(56) References Cited

U.S. PATENT DOCUMENTS

| | | | | |
|---|---|---|---|---|
| 4,439,494 A | * | 3/1984 | Olson | 428/412 |
| 5,120,780 A | * | 6/1992 | Martino et al. | 524/188 |
| 5,132,377 A | * | 7/1992 | Nakano et al. | 525/509 |
| 5,627,252 A | * | 5/1997 | De La Croi Habimana | 528/26 |
| 6,268,456 B1 | * | 7/2001 | Gregorovich et al. | 528/35 |
| 2006/0147916 A1 | * | 7/2006 | Ishibashi et al. | 435/6 |
| 2006/0199923 A1 | * | 9/2006 | Akiba et al. | 525/476 |

OTHER PUBLICATIONS

Abstract for an article entitled "Synthesis and Properties of Alkoxysilane Compounds Derived from 12-Hydroxystearic acid" published in Kagaku to Kogyo (2002), 76(9), 456-465.*

Abstract for the article entitled "A Novel Method for Preparation and Characterization of Restricted-Access Media-Alyl-Diol-Silica" published in Journal of Liquid Chromatography & Related Technologies (2001), 24(14), 2197-2208.*

* cited by examiner

*Primary Examiner*—Marc S. Zimmer
(74) *Attorney, Agent, or Firm*—Kevin S. Dobson

(57) ABSTRACT

Organosilicon compounds are described which are prepared from epoxy-functional silanes and monocarboxylic acids. The compounds are useful in coatings, adhesives, and sealants, and the like.

7 Claims, No Drawings

PREPARATION AND USE OF REACTIVE ORGANOSILICON COMPOUNDS

FIELD OF THE INVENTION

This invention relates to the preparation of organosilicon compounds and their use as reactive materials in various moisture cure applications, such as adhesives, sealants and coatings.

TECHNICAL BACKGROUND

Reactive organosilicon compounds have found widespread use as reactive film forming materials and/or adhesion promoters in various moisture cure applications, including, in adhesives, sealants and coatings. Such compounds have been found particularly useful in high performance coatings used for finishing automobile and truck exteriors.

Of particular interest to makers and users of coatings is to lower the volatile organic content (VOC) of such coatings, particularly to meet increasingly stringent environmental regulations. Various possible approaches for solving VOC problems are, therefore, of significant interest in the relevant industries.

Applicants have found that lower VOC compositions also having improved adhesion to various subsequently applied coatings can be obtained by use of certain novel reactive organosilicon compounds.

Previous attempts to lower the VOC and improve adhesion with organosilicon compounds have been tried. For example, U.S. Pat. No. 6,268,456 discloses the use of organosilicon compounds derived from epoxy-functional silanes and polycarboxylic acids. Such materials, however, are generally unstable, i.e., viscosity gradually increases up to gelation, and are therefore less useful in lowering VOCs because of their high viscosity.

SUMMARY OF THE INVENTION

The invention concerns an organosilicon compound, which is the reaction product of an epoxy-functional silane with a monocarboxylic acid, preferably a cycloaliphatic monocarboxylic acid. More preferably, the invention concerns the reaction product of a carboxylic acid of the formula

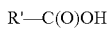

with an epoxy-functional silane of the formula

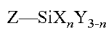

the reaction product having a number average molecular weight more than 200 and less than about 5,000, preferred less than about 2,500, more preferred less than about 1,500;
wherein:

R' is selected from the group consisting of a) $C_2$ to $C_{20}$ alkyl, cycloaliphatic or cycloaromatic rings, each optionally substituted with at least one member selected from the group consisting of O, N, P and S;

b) two or more cycloaliphatic or aromatic rings connected to each other through a covalent bond or through an alkylene group of 1 to 5 carbon atoms, or through a heteroatom, or fused together to share two or more carbon atoms, each optionally substituted with at least one member selected from the group consisting of O, N, P and S; and c) linear polyester, branched polyester, linear and branched polyester, polyacrylate, polyolefin, polyether, polycarbonate, polyurethane, or polyamide, or other "low molecular weight polymer moiety" having a weight average molecular weight no more than about 5000;

X is independently selected from the group consisting of alkoxy containing 1 to 20 carbon atoms, carboxyloxy containing 1 to 20 carbon atoms, phenoxy, halogen, amine, amide, urea, imidazole, carbamate, ketoximine, oxazolidinone and a combination thereof;

Y is selected from the group consisting of alkyl of 1 to 12 carbon atoms, or aromatic rings or hydrogen;

Z is an epoxy group containing $C_3$ to $C_{20}$ carbon atoms, optionally substituted with O or P; and n is 1, 2 or 3.

The reactive compound that is preferably formed has an average of one hydroxyl group and one reactive silane group. By "reactive silane group" it is meant a group which contains at least one, preferably two to three, hydrolyzable (i.e., moisture curable) X groups (as defined above) attached to silicon atom. Preferably, in the formulas above, R' is a cycloaliphatic ring, X is independently selected from a $C_1$ to $C_3$ alkoxy group, Z is an epoxy group containing $C_3$ to $C_{20}$ carbon atoms; and n is 3.

The invention also includes a method for preparing such compounds, and use of such compounds in various moisture cure applications, such as in liquid adhesives, sealants and coatings. Also disclosed is an article, such as a vehicle body or a part thereof, treated with the forgoing adhesive, sealant or coating.

DETAILED DESCRIPTION OF THE PREFERRED EMBODIMENTS

The organosilicon reactive compounds described herein are useful as described above wherein the hydroxyl reactive group as well as the reactive groups on silicon (such as alkoxy; carboxyloxy; amine), may be hydrolyzed in the presence of atmospheric moisture or otherwise reacted to improve adhesion, provide crosslinks, etc. They are especially useful in coatings, where they may be used as reactive materials for the crosslinking of functional group (such as hydroxyl; melamine; isocyanate; silane) containing monomers, oligomers, and/or polymers. It is believed that these compounds not only provide this "reactive" functionality in coatings, but in the preferred embodiment where a cycloaliphatic monocarboxylic acid is used, because of the presence of the cycloaliphatic group, they provide a good balance of (higher) hardness, flexibility, scratch resistance, acid etch resistance, and crosslinking speed.

The silicon compounds based on this invention are most conveniently prepared by reacting epoxy-functional silane of the above formula with monocarboxylic acid of the above formula at the molar ratio from about 0.5 to 5, more preferably from about 0.7 to 2.0 at elevated temperatures ranging from about 25 to 150° C. in an inert atmosphere. Reaction is continued until the desired acid number and conversion are reached.

The resultant silicon compounds are preferably characterized by a weight average molecular weight from about 200 to 5,000, more preferably from about 300 to 1,500, an acid number in the range from about 0 to 50 (mg KOH/g resin solids), preferably from about 0 to 30, and even more preferably from about 0 to 20. These materials have been shown to be stable, i.e., not rheologically active, and are able to maintain a low viscosity of about 0.1 to 100 poise, preferably of about 0.1 to 30 poise and even more preferably about 0.1 to 10 poise determined by I.C.I cone & plate viscometer at 25° C. for an extended period of time of over 3 months at ambient temperature. (All molecular weights disclosed herein are determined by gel permeation chromatography using a polystyrene standard.)

Typically useful epoxy-functional silanes are (3-glycidoxypropyl)trimethoxysilane, (3-glycidoxypropyl)triethoxysilane, (3-glycidoxypropyl)methyldimethoxysilane, (3-glycidoxypropyl)methyldiethoxysilane, (3-glycidoxypropyl)dimethylmethoxysilane, (3-glycidoxypropyl)dimethylethoxysilane, 5,6-epoxyhexyltrimethoxysilane, 5,6-epoxyhexyltriethoxysilane, 5,6-epoxyhexylmethyldimethoxysilane, 5,6-epoxyhexylmethyldiethoxysilane, 5,6-epoxyhexyldimethylmethoxysilane, 5,6-epoxyhexyldimethylethoxysilane.

Typically useful monocarboxylic acids are cycloaliphaticcarboxylic acids, and substituted cycloaliphaticcarboxylic acids such as cyclohexanecarboxylic acid, cyclopropanecarboxylic acid, cyclobutanecarboxylic acid, cyclopentanecarboxylic acid, cycloheptanecarboxylic acid, adamantanecarboxylic acid, methyl-cyclohexanecarboxylic acids.

Monocarboxylic acids containing cycloaliphatic groups are generally preferred.

As indicated above, the presently disclosed reactive organosilicon compounds are useful in coatings, especially automotive coatings, either clearcoat or color coat compositions. Such a coating composition, before and/or after application to a substrate, must comprise a film-forming portion, comprising polymeric components, which is referred to as the "binder" or "binder solids" and is dissolved, emulsified or otherwise dispersed in an organic solvent or liquid carrier. The binder solids generally include all the components that contribute to the solid organic portion of the cured composition. Generally, catalysts, pigments, and non-polymeric chemical additives such as stabilizers are not considered part of the binder. Non-binder solids other than pigments usually do not amount to more than about 5-10% by weight of the composition. In this disclosure, the term binder includes the reactive silane compound, and all other optional film-forming components including various other polymers, oligomers and crosslinking agents.

The coating composition preferably contains about 50-100% by weight of the binder and about 0-50% by weight of the organic solvent carrier, which is typically referred to as a high-solids coating. The binder of the coating composition may comprise up to 100% of the above reactive dual functional organosilicon compounds (containing both reactive silane and hydroxyl functionalities) preferably about 0.1-20%, more preferably about 1-10%, even more preferably about 2 to 5% by weight of the binder. (In the present invention, the organosilicon compounds prepared above are also referred to herein as "dual functional" compounds, since they contain both reactive silane and hydroxyl functionalities.)

The coating composition can include a number of other ingredients to enhance preparation of the composition as well as improve final properties of the coating composition and the finish.

For example, the coating composition may optionally also contain a silane-functional polymer (pref. silane containing acrylics) and/or a hydroxy-functional polymer (Preferably polyol containing acrylics), as for example, disclosed in U.S. Pat. No. 5,244,959 hereby incorporated by reference in its entirety. For example, it is often desirable to include about 20 to 90%, preferably 20 to 60%, by weight of the composition, of a film-forming reactive silane polymer, which is different from the silane compound described above. Such polymer typically has a number average molecular weight of about 500 to 10,000.

The silane polymer is typically the polymerization product of about 30-95%, preferably 40-60%, by weight of ethylenically unsaturated nonsilane containing monomers and about 5-70%, preferably 40-60%, by weight of ethylenically unsaturated silane-containing monomers, based on the weight of the organosilane polymer. Suitable ethylenically unsaturated nonsilane containing monomers are alkyl acrylates, alkyl methacrylates and mixtures thereof, where the alkyl groups have 1-12 carbon atoms, preferably 3-8 carbon atoms.

Suitable alkyl methacrylate monomers used to form the organosilane polymer are methyl methacrylate, ethyl methacrylate, propyl methacrylate, butyl methacrylate, isobutyl methacrylate, pentyl methacrylate, hexyl methacrylate, octyl methacrylate, nonyl methacrylate, lauryl methacrylate and the like. Suitable alkyl acrylate monomers include methyl acrylate, ethyl acrylate, propyl acrylate, butyl acrylate, isobutyl acrylate, pentyl acrylate, hexyl acrylate, octyl acrylate, nonyl acrylate, lauryl acrylate and the like. Cycloaliphatic methacrylates and acrylates also can be used, such as isobornyl methacrylate, cyclohexyl methacrylate, trimethylcyclohlexyl methacrylate, trimethylcyclohexyl acrylate, iso-butyl cyclohexyl methacrylate, t-butyl cyclohexyl acrylate, and t-butyl cyclohexyl methacrylate. Aryl acrylate and aryl methacrylates also can be used, such as benzyl acrylate and benzyl methacrylate. Mixtures of two or more of the above-mentioned monomers are also suitable.

In addition to alkyl acrylates and methacrylates, other polymerizable nonsilane-containing monomers, up to about 50% by weight of the polymer, can be used in the acrylosilane polymer for the purpose of achieving the desired properties such as hardness; appearance; mar, etch and scratch resistance, and the like. Exemplary of such other monomers are styrene, methyl styrene, acrylamide, acrylonitrile, methacrylonitrile, and the like.

A silane-containing monomer useful in forming the acrylosilane polymer is an alkoxysilane having the following structural formula:

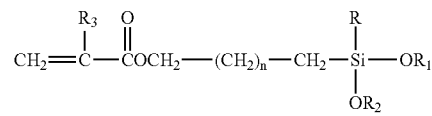

wherein R is either $CH_3$, $CH_3CH_2$, $CH_3O$, or $CH_3CH_2O$; $R_1$ and $R_2$ are independently $CH_3$ or $CH_3CH_2$; and $R_3$ is either H, $CH_3$, or $CH_3CH_2$; and n is 0 or a positive integer from 1 to 10. Preferably, R is $CH_3O$ or $CH_3CH_2O$, $R_1$ and $R_2$ are $CH_3$ or $CH_3CH_2$ and n is 1.

Typical examples of such alkoxysilanes are the acryloxy alkyl silanes, such as gamma-acryloxypropyl-trimethoxysilane and the methacryloxy alkyl silanes, such as gamma-methacryloxypropyltrimethoxysilane, and gamma-methacryloxypropyltris(2-methoxyethoxy)silane.

Other suitable alkoxysilane monomers have the following structural formula:

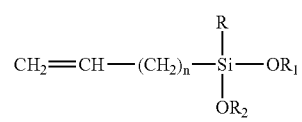

wherein R, $R_1$ and $R_2$ are as described above and n is 0 or a positive integer from 1 to 10. Examples of such alkoxysilanes are the vinylalkoxysilanes, such as vinyltrimethoxysilane, vinyltriethoxysilane and vinyltris(2-methoxyethoxy)

silane. Other examples of such alkoxysilanes are the allylalkoxysilanes such as allyltrimethoxysilane and allyltriethoxysilane.

Other suitable silane-containing monomers are acyloxysilanes, including acryloxysilane, methacryloxysilane and vinyl silanes, such as vinylmethyldiacetoxysilane, acryloxypropyltriacetoxysilane, and methacryloxypropyltriacetoxysilane. Of course, mixtures of the silane-containing monomers are also suitable.

Silane functional macromonomers also can be used in forming the silane polymer. These macromonomers are the reaction product of a silane-containing compound, having a reactive group such as epoxide, amine or isocyanate, with an ethylenically unsaturated non-silane-containing monomer having a reactive group, typically a hydroxyl, carboxyl, isocyanate or an epoxide group, that is co-reactive with the silane monomer. An example of a useful macromonomer is the reaction product of a hydroxy functional ethylenically unsaturated monomer such as a hydroxyalkyl acrylate or methacrylate having 1-8 carbon atoms in the alkyl group and an isocyanatoalkyl alkoxysilane such as isocyanatopropyltriethoxysilane.

Typical of such silane-functional macromonomers are those having the following structural formula:

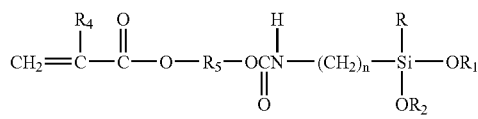

wherein R, $R_1$, and $R_2$ are as described above; $R_4$ is H or $CH_3$, $R_5$ is an alkylene group having 1-8 carbon atoms and n is a positive integer from 1-8.

The silane materials can also be oligomeric in nature. These materials are well known in that art.

Mixtures of polymeric and oligomeric hydroxy functional silane compounds may also be utilized in the present invention.

In addition to the organosilane polymer, other film-forming and/or crosslinking solution polymers may be included in the present application. Examples include conventionally known acrylics, cellulosics, aminoplasts, urethanes, polyesters, epoxides or mixtures thereof. One preferred optional film-forming polymer is a polyol, for example an acrylic polyol solution polymer of polymerized monomers. Such monomers may include, for example, alkyl acrylates and/or methacrylates and, in addition, hydroxy alkyl acrylates or methacrylates. The polyol polymer preferably has a hydroxyl number of about 50-200 and a weight average molecular weight of about 1,000-200,000 and more preferably about 1,000-20,000.

To provide the hydroxy functionality in the polyol, up to about 90% by weight, preferably 20 to 50%, of the polyol comprises hydroxy functional polymerized monomers. Suitable monomers include hydroxy alkyl acrylates and methacrylates, for example, hydroxyethyl acrylate, hydroxypropyl acrylate, hydroxyisopropyl acrylate, hydroxybutyl acrylate, hydroxyethyl methacrylate, hydroxypropyl methacrylate, hydroxyisopropyl methacrylate, hydroxybutyl methacrylate, and the like, and mixtures thereof.

Other polymerizable non-hydroxy containing monomers may be included in the polyol polymer, in an amount up to about 90% by weight, preferably 50 to 80%. Such polymerizable monomers include, for example, styrene, methylstyrene, acrylamide, acrylonitrile, methacrylonitrile, methacrylamide, methylol methacrylamide, methylol acrylamide, and the like, and mixtures thereof.

Another optional component of the coating composition of the present invention is, in addition to the above polymeric components, a dispersed polymer. Polymers dispersed in an organic (substantially non-aqueous) medium have been variously referred to, in the art, as a non-aqueous dispersion (NAD) polymer, a microgel, a non-aqueous latex, or a polymer colloid. See generally, Poehlin et at., editor, Science and Technology of Polymer Colloids, Volume 1, pages 40-50 (1983); El-Asser, editor, Future Directions in Polymer Colloids, pages 191-227 (1987); Barrett, Dispersion Polymerization in Organic Media (John Wiley 1975). See also U.S. Pat. Nos. 4,147,688; 4,180,489; 4,075,141; 4,415,681; and 4,591,533, hereby incorporated by reference. Microgel particles, necessarily cross-linked, have been used for years as impact modifiers for plastics, as rheology controllers for coatings, and in basecoats, to permit wet-on-wet application of paints.

The coating composition preferably further includes a crosslinking agent reactive with the reactive organosilicon compound and, optionally, with other materials, such optional polyol component, in the coating composition to form a faster curing coating composition. The crosslinking agent preferably includes at least two, and preferably more than two, groups that are reactive with the hydroxyl group on the reactive dual functional silicon compound. The coating composition preferably includes, as part of the binder, about 5-50%, more preferably about 20-40% by weight crosslinker, based on the weight of the binder Illustrative examples of crosslinkers include, without limitation, aminoplast resins such as melamine/formaldehyde adducts or phenoplast resins such as phenol/formaldehyde adducts, as well as other materials having active methylol or methylalkoxy groups, unblocked polyisocyanates, blocked polyisocyanates, compounds having silane groups, polyepoxide materials, and compounds having anhydride groups; and mixtures thereof. Among preferred curing agent compounds are melamine formaldehyde resin (including monomeric or polymeric melamine resin and partially or fully alkylated melamine resin), blocked or unblocked polyisocyanates, urea resins (e.g., methylol ureas such as urea formaldehyde resin, alkoxy ureas such as butylated urea formaldehyde resin), polyanhydrides (e.g., polysuccinic, polymaleic anhydride (co)polymers), and combinations of these. In the case of crosslinking agents such as the unblocked polyisocyanates that do not have long-term stability at room temperatures when mixed with the reactive silicon material (and any other reactive component of the coating composition), the coating is formulated as a two-component coating composition, also known as two-pack or 2K coating composition, with the crosslinking agent being segregated in a container separate from the components with which it reacts.

Examples of suitable melamine formaldehyde resins of the forgoing type which are generally preferred are commercially available from Cytec Industries, Inc. under the trademark Cymel® and from Solutia, Inc. under the trade name Resimene®.

Examples of suitable polyisocyanates include, without limitation, alkylene polyisocyanates such as hexamethylene diisocyanate, 2,2,4- and/or 2,4,4-trimethylhexamethylene diisocyanate, dodecamethylene diisocyanate, 1,4-diisocyanatocyclohexane, 1-isocyanato-3,3,5-trimethyl-5-isocyanatomethylcyclohexane (IPDI), 2,4'- and/or 4,4'-diisocyanatodicyclohexylmethane, 3-isocyanato-methyl-3,5,5-trimethyl cyclohexyl isocyanate, aromatic polyisocyanates such as 2,4'- and/or 4,4'-diisocyanatodiphenylmethane, 2,4- and/or 2,6-diisocyanatotoluene, naphthylene diisocyanate, and mixtures of these polyisocyanates. It is preferred to use the known derivatives or adducts of those monomeric polyisocyanates. Examples include biuret-group-containing polyisocyanates; isocyanurate-group-containing polyisocyanates; urethane-group-containing polyisocyanates; carbodiimide group-containing polyisocyanates; allophanate group-containing polyisocyanates; and uretdione group-containing polyisocyanates. Examples of blocking agents include, without limitation, phenols, thiols, oximes, caprolactams, and secondary aromatic amines.

An effective amount of catalyst, typically less than 5% by weight of the composition, is typically added to catalyze the crosslinking of the silane moieties of the silane polymer with itself and with other components of the composition, including the dispersed polymer. Typical of such catalysts are dibutyltin dilaurate, dibutyltin diacetate, dibutyltin dioxide, dibutyltin dioctoate, tin octoate, titanium alkoxides, aluminum titanate, aluminum chelates, zirconium chelate and the like. Tertiary amines and acids or combinations thereof are also useful for catalyzing silane bonding. Preferably, these catalysts are used in the amount of about 0.1 to 5.0% by weight of the composition.

To improve weatherability of a clear finish produced by the present coating composition, an ultraviolet light stabilizer or a combination of ultraviolet light stabilizers can be added in the amount of about 0.1-5% by weight, based on the weight of the binder. Such stabilizers include ultraviolet light absorbers, screeners, quenchers, and specific hindered amine light stabilizers. Also, an antioxidant can be added, in the about 0.1-5% by weight, based on the weight of the binder.

Typical ultraviolet light stabilizers that are useful include benzophenones, triazoles, triazines, benzoates, hindered amines and mixtures thereof. Specific examples of ultraviolet stabilizers are disclosed in U.S. Pat. No. 4,591,533, the entire disclosure of which is incorporated herein by reference.

The composition may also include other conventional formulation additives such as flow control agents, for example, such as Resiflow® S (polybutylacrylate), BYK® 320 and 325 (high molecular weight polyacrylates); rheology control agents, such as fumed silica; water scavengers such as tetraorthosilicate, trimethylorthoformate, triethylorthoformate and the like.

When the present composition is used as a clearcoat (topcoat) over a pigmented colorcoat (basecoat) to provide a basecoat/clearcoat finish, small amounts of pigment can be added to the clear coat to eliminate undesirable color in the finish such as yellowing.

The present composition also can be pigmented and used as the colorcoat, or as a monocoat or even as a primer or primer surfacer. The composition has excellent adhesion to a variety of substrates, such as previously painted substrates, cold rolled steel, phosphatized steel, and steel coated with conventional primers by electrodeposition. The present composition exhibits excellent adhesion to primers, for example, those that comprise crosslinked epoxy polyester and various epoxy resins, as well as alkyl resin repair primers. The present composition can be used to coat plastic substrates such as polyester reinforced fiberglass, reaction injection-molded urethanes and partially crystalline polyamides.

When the present coating composition is used as a basecoat, typical pigments that can be added to the composition include the following: metallic oxides such as titanium dioxide, zinc oxide, iron oxides of various colors, carbon black, filler pigments such as talc, china clay, barytes, carbonates, silicates and a wide variety of organic colored pigment such as quinacridones, copper phthalocyanines, perylenes, azo pigments, indanthrone blues, carbazoles such as carbazole violet, isoindolinones, isoindolones, thioindigo reds, benzimidazolinones, metallic flake pigments such as aluminum flake and the like.

The pigments can be introduced into the coating composition by first forming a mill base or pigment dispersion with any of the aforementioned polymers used in the coating composition or with another compatible polymer or dispersant by conventional techniques, such as high speed mixing, sand grinding, ball milling, attritor grinding or two roll milling. The mill base is then blended with the other constituents used in the coating composition.

Conventional solvents and diluents may be used, preferably in minimal amounts, to disperse and/or dilute the above mentioned polymers to obtain the present coating composition. Typical solvents and diluents include toluene, xylene, butyl acetate, acetone, methyl isobutyl ketone, methyl ethyl ketone, methanol, isopropanol, butanol, hexane, acetone, ethylene glycol, monoethyl ether, VM and P naphtha, mineral spirits, heptane and other aliphatic, cycloaliphatic, aromatic hydrocarbons, esters, ethers and ketones and the like.

The coating composition can be applied by conventional techniques such as spraying, electrostatic spraying, dipping, brushing, flowcoating and the like. The preferred techniques are spraying and electrostatic spraying. After application, the composition is typically baked at 100-150° C. for about 15-30 minutes to form a coating about 0.1-3.0 mils thick. When the composition is used as a clearcoat, it is applied over the colorcoat which may be dried to a tack-free state and cured or preferably flash dried for a short period before the clearcoat is applied. The colorcoat/clearcoat finish is then baked as mentioned above to provide a dried and cured finish.

It is customary to apply a clear topcoat over a basecoat by means of a "wet-on-wet" application, i.e., the topcoat is applied to the basecoat without curing or completely drying the basecoat. The coated substrate is then heated for a predetermined time period to allow simultaneous curing of the base and clear coats.

The coating composition can be formulated as a one-package or two-package system that has an extended shelf life.

The reactive silicon compounds are also useful as an additive in moisture cure adhesives and sealants, especially in polyurethane windshield bonding sealant and adhesive compositions, such as those described in U.S. Pat. No. 5,852,137, hereby incorporated by reference.

The following Examples illustrate the invention. All parts and percentages are on a weight basis unless otherwise indicated.

EXAMPLE 1

Preparation of a dual functional silane (major idealized product represented in structure I) from an epoxy-functional silane and cycloaliphatic acid

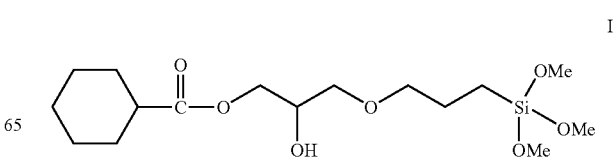

A mixture of 3-glycidoxypropyltrimethoxysilane (3GPTMS) (120 g, 0.51 mole) and cylcohexnecarboxylic acid (50 g, 0.39 mole) was reacted in a closed container in an oven at around 100° C. The reaction was followed by the acid number decrease. The acid numbers were 59 after 16 hours, 50 after 38 hours, 42 after 56 hours, 38 after 75 hours and 31 after 103 hours. A yield of 155 g product was obtained. The product was colorless liquid having a viscosity of 45 cP, containing <15% of starting 3-GPTMS monomer, as measured by GC. The product theoretical hydroxy equivalent weight was 436 and silane equivalent weight was 336. The oligomers showed good stability, with a viscosity of 50 cP after 99 days stored in a closed container under nitrogen at room temperature.

EXAMPLE 2

Preparation of a dual functional silane (major idealized product represented in structure I) from an epoxy-functional silane and cycloaliphatic acid A mixture of 3-glycidoxypropyltrimethoxysilane (3GPTMS) (480 g, 2.04 mole) and cylcohexnecarboxylic acid (200 g, 1.56 mole) was reacted in a closed container in an oven at around 100° C. The reaction was followed by the acid number decrease. The acid number was 30 after 160 hours. The product was colorless liquid having a viscosity of 0.5 Poise. The product theoretical hydroxy equivalent weight was 436 and silane equivalent weight was 336. The oligomers showed good stability, with a viscosity of 1.0 Poise after 20 months stored in a closed container under nitrogen at room temperature.

EXAMPLE 3

Preparation of a dual functional silane (major idealized product represented in structure I) from an epoxy-functional silane and cycloaliphatic acid A mixture of 3-glycidoxypropyltrimethoxysilane (3GPTMS) (240 g, 1.02 mole) and cylcohexnecarboxylic acid (100 g, 0.78 mole) was reacted in a closed container in an oven at around 100° C. The reaction was followed by the acid number decrease. The acid number was 20 after 211 hours. The product was colorless liquid having a viscosity of 2.0 Poise. The product theoretical hydroxy equivalent weight was 436 and silane equivalent weight was 336. The oligomers showed good stability, with a viscosity of 3.0 Poise after 3 months, 3.5 Poise after 5 month and 2.2 Poise after 21 months stored in a closed container under nitrogen at room temperature.

EXAMPLE 4

Preparation of a dual functional silane (major idealized product represented in structure I) from an epoxy-functional silane and cycloaliphatic acid A mixture of 3-glycidoxypropyltrimethoxysilane (3GPTMS) (120 g, 0.51 mole) and cylcohexnecarboxylic acid (50 g, 0.39 mole) was reacted in a closed container in an oven at around 100° C. The reaction was followed by the acid number decrease. The acid numbers were 60 after 64 hours, 50 after 86 hours, 42 after 105 hours, 38 after 123 hours and 31 after 151 hours. The product was colorless liquid having a viscosity of 0.5 Poise. The product theoretical hydroxy equivalent weight was 436 and silane equivalent weight was 336. The oligomers showed good stability, with a viscosity of 0.5 Poise after 3 months and 5.8 Poise after 24 months stored in a closed container under nitrogen at room temperature.

EXAMPLE 5

Preparation of a dual functional silane (major idealized product represented in structure I) from an epoxy-functional silane and cycloaliphatic acid A mixture of 3-glycidoxypropyltrimethoxysilane (3GPTMS) (120 g, 0.51 mole) and cylcohexnecarboxylic acid (50 g, 0.39 mole) was reacted in a closed container in an oven at around 100° C. The reaction was followed by the acid number decrease. The acid numbers were 101 after 18 hours, 77 after 39 hours, 34 after 106 hours and 29 after 126 hours. The product was colorless liquid having a viscosity of 0.8 Poise. The product theoretical hydroxy equivalent weight was 436 and silane equivalent weight was 336. The oligomers showed good stability, with a viscosity of 1.8 Poise after 24 months stored in a closed container under nitrogen at room temperature.

COMPARATIVE EXAMPLE 1

Preparation of a dual functional silane from an epoxy-functional silane and acyclicaliphatic dicarboxylic acid A mixture of 3-glycidoxypropyltrimethoxysilane (3GPTMS) (5 g, 0.021 mole) and glutaric acid (1.4 g, 0.011 mole) was reacted in a closed container in an oven at around 100° C. The reaction was followed by the acid number decrease. The acid numbers were 106 after 22 hours and 76 after 46 hours, but viscosity was too high >100 Poise.

COMPARATIVE EXAMPLE 2

Preparation of a dual functional silane from an epoxy-functional silane and cycloaliphatic dicarboxylic acid A mixture of hexahydro-4-methylphtalic anhydride (1 g, 0.0059 mole) and water (0.1 g, 0.0056 mole) was reacted in a closed container in an oven at around 60° C. for 55 min. Then 3-glycidoxypropyltrimethoxysilane (3GPTMS) (2.54 g, 0.0096 mole) was added and reacted in a closed container in an oven at around 100° C. After 140 hours viscosity of the reaction mixture became too high >100 Poise.

COMPARATIVE EXAMPLE 3

Preparation of a dual functional silane from an epoxy-functional silane and cycloaliphatic dicarboxylic acid A mixture of hexahydro-4-methylphtalic anhydride (100 g, 0.59 mole) and 1,4-cyclohexanedimethanol (40 g, 0.28 mole) was reacted in a round bottom flask with a stirrer under nitrogen blanket at around 100° C. for 1 hour. Then 3-glycidoxypropyltrimethoxysilane (3GPTMS) (155 g, 0.66 mole) and tetrabutylammonium hydroxide (5 g 1.0 M solution in methanol, 0.005 mole) were added and reacted at around 100° C. After 5 hours viscosity of the reaction mixture became too high >100 Poise.

COMPARATIVE EXAMPLE 4

Preparation of a dual functional silane from an epoxy-functional silane and cycloaliphatic dicarboxylic acid A mixture of hexahydro-4-methylphtalic anhydride (100 g, 0.59 mole) and 4,4'-isopropylidenedicyclohexanol (70 g, 0.29 mole) was reacted in a round bottom flask with a stirrer under nitrogen blanket at around 100° C. for 1 hour. Then 3-glycidoxypropyltrimethoxysilane (3GPTMS) (155 g, 0.66 mole) and tetrabutylammonium hydroxide (5 g 1.0 M solution in methanol, 0.005 mole) were added and reacted at around 100° C. After 4 hours viscosity of the reaction mixture became too high >100 Poise.

EXAMPLE 6

Preparation of a model clear coating composition containing a dual functional silane from an epoxy-functional silane and isocyanates A model clearcoat composition useful for screening and demonstrating utility of a new dual functional silane for coatings application was prepared by mixing silane from example 2 (200 g, 0.46 mole of HO), Desmodur® N3300A (isocyanate trimer of hexamethylene diisocyanate, 94 g, 0.56 mole of active iso groups) and dibutyltin dilaurate (0.02 g). The reaction mixture showed a good pot life with viscosity of 6 Poise after 4 hours and 11 Poise after 26 hours stored in a closed container under nitrogen at room temperature.

EXAMPLE 7

Preparation of a model clear coating composition containing a dual functional silane from an epoxy-functional silane and isocyanates A model clearcoat composition useful for screening and demonstrating utility of a new dual functional silane for coatings application was prepared by mixing silane from example 2 (120 g, 0.33 mole of HO), Desmodur N3300A (isocyanate trimer of hexamethylene diisocyanate, 170 g, 1.0 mole of active iso groups) and dibutyltin dilaurate (0.02 g). The coating composition showed a good pot life with viscosity of 11.5 Poise after 4 hours, 17.5 Poise after 26 hours and 57 Poise after 80 days stored in a closed container under nitrogen at room temperature.

EXAMPLE 8

Preparation of a model clear coating composition containing a dual functional silane from an epoxy-functional silane and isocyanates A model clearcoat composition useful for screening and demonstrating utility of a new dual functional silane for coatings application was prepared by mixing silane from example 4 (90 g, 0.25 mole of HO), Desmodur N3300A (isocyanate trimer of hexamethylene diisocyanate, 42 g, 0.25 mole of active iso groups) and dibutyltin dilaurate (0.02 g). The coating composition showed a good pot life with viscosity of 6.0 Poise after 1.5 hours and 15.5 Poise after 29 hours stored in a closed container under nitrogen at room temperature. The coating composition showed good reactivity when exposed to an ambient moisture and temperature measured by viscosity changes of several drops placed on I.C.I. cone & plate viscometer: 1.5 Poise at start, 5.5 Poise after 5 min., 7.0 Poise after 10 min., 13 Poise after 20 min., 20 Poise after 30 min., 31.5 Poise after 40 min., 44.5 Poise after 50 min. and 62 poise after 60 min.

EXAMPLE 9

Preparation of a model clear coating containing a dual functional silane from an epoxy-functional silane and isocyanates A model clearcoat composition useful for screening and demonstrating utility of a new dual functional silane for coatings application was prepared by mixing silane from example 4 (50 g, 0.14 mole of HO), Desmodur N3300A (isocyanate trimer of hexamethylene diisocyanate, 70 g, 0.42 mole of active iso groups) and dibutyltin dilaurate (0.02 g). The coating composition showed a good pot life with viscosity of 11 Poise after 1.5 hours, 24 Poise after 29 hours and 57 poise after 100 days stored in a closed container under nitrogen at room temperature. The coating composition showed good reactivity when exposed to an ambient moisture and temperature measured by viscosity changes of several drops placed on I.C.I. cone & plate viscometer: 45 Poise at start, 52 Poise after 5 min., 56 Poise after 10 min., 72 Poise after 20 min., 76 Poise after 30 min., 90 Poise after 60 min., and over 100 poise after 90 min.

EXAMPLE 10

Preparation of a model clear coating containing a dual functional silane from an epoxy-functional silane and isocyanates A model clearcoat composition useful for screening and demonstrating utility of a new dual functional silane for coatings application was prepared by mixing silane from example 5 (1.0 g, 0.0029 mole of HO), Desmodur N3300A (isocyanate trimer of hexamethylene diisocyanate, 0.45 g, 0.0027 mole of active iso groups) and dibutyltin dilaurate (0.01 g). The coating composition showed a good pot life with viscosity of 37 Poise after 20 hours stored in a closed container under nitrogen at room temperature. The coating composition was applied as a coating on a phosphatized steel panel using 2 mil film applicator. The coating was tack free after 6-8 hours at ambient conditions.

EXAMPLE 11

Preparation of a model clear coating containing a dual functional silane from an epoxy-functional silane and isocyanates A model clearcoat composition useful for screening and demonstrating utility of a new dual functional silane for coatings application was prepared by mixing silane from example 5 (2.0 g, 0.0059 mole of HO), Desmodur N3300A (isocyanate trimer of hexamethylene diisocyanate, 0.9 g, 0.0054 mole of active iso groups) and dibutyltin dilaurate (0.002 g). The coating composition showed a good pot life with viscosity of 14 Poise after 20 hours stored in a closed container under nitrogen at room temperature. The coating composition was applied as a coating on a phosphatized steel panel using 2 mil film applicator. The coating showed good hardness of 45 PZ (Persoz) developed at ambient conditions when measured after 3 weeks.

EXAMPLE 12

Preparation of a model clear coating containing a dual functional silane from an epoxy-functional silane and isocyanates A model clearcoat composition useful for screening and demonstrating utility of a new dual functional silane for coatings application was prepared by mixing silane from example 5 (2.0 g, 0.0059 mole of HO), Desmodur N3300A (isocyanate trimer of hexamethylene diisocyanate, 2.7 g, 0.0162 mole of active iso groups) and dibutyltin dilaurate (0.002 g). The coating composition showed a good pot life with viscosity of 35 Poise after 20 hours stored in a closed container under nitrogen at room temperature. The coating composition was applied as a coating on a phosphatized steel panel using 2 mil film applicator. The coating showed good hardness of 135 PZ (Persoz) developed at ambient conditions when measured after 3 weeks.

EXAMPLE 13

Preparation of a model clear coating containing a dual functional silane from an epoxy-functional silane and isocyanates A model clearcoat composition useful for screening and demonstrating utility of a new dual functional silane for coatings application was prepared by mixing silane from example 5 (2.0 g, 0.0059 mole of HO), Desmodur N3300A (isocyanate trimer of hexamethylene diisocyanate, 1.8 g, 0.0108 mole of active iso groups) and dibutyltin dilaurate (0.002 g). The coating composition showed a good pot life with viscosity of 22 Poise after 20 hours stored in a closed container under nitrogen at room temperature. The coating composition was applied as a coating on a phosphatized steel panel using 2 mil film applicator. The coating showed good hardness of 61 PZ (Persoz) developed at ambient conditions when measured after 3 weeks.

EXAMPLE 14

Preparation of a clear coating containing a dual functional silane from an epoxy-functional silane An automotive clearcoat composition useful for finishing the exteriors of automobiles and trucks was prepared as follows

| Ingredients | Example 14 Parts by Weight |
|---|---|
| PART 1 | |
| Silane[1] | 5 |
| 2-Ethyl-1,3-hexanediol | 4 |
| 2-Ethylhexanol | 2 |
| Melamine[2] | 35.22 |
| UV/HALS[3] | 7.5 |
| Flow Aid[4] | 1 |
| Hyperbranched copolyester[5] | 11.76 |
| Acid Catalyst[6] | 2 |
| Bismuth Catalyst[7] | 0.29 |
| PART 2 | |
| Isocyanate[8] | 44 |
| Total | 112.78 |

Table Footnotes
[1]Silane from Example 1
[2]Resimene ® CE8230 melamine (90% solid) supplied by Solutia Inc., St Louis, MO.
[3]40% Solution in 2-ethylhexyl acetate of Tinuvin ® 384/Tinuvin ® 292 supplied by Ciba Speciality Chemicals, Tarryton, NY) 2:1 ratio.
[4]10% Disperlon ® LC 955 flow additive in aromatic hydrocarbon supplied by King Industries, Norwalk, Connecticut.
[5]85% Hyperbranched copolyester solution prepared in accordance with the procedure described in WO 03/070844 at page 35, lines 1-2 and page 36, lines 1-2 in connection with the Highly Branched Copolyester Polyol-Soluition 5, all of which is incorporated by reference.
[6]Nacure ® 5543 25% amine-blocked dodecylbenzene sulfonic acid catalyst supplied by King Industries, Norwalk, Connecticut.
[7]Kcat ® XC 8203 68% bismuth catalyst supplied by King Industries, Norwalk, Connecticut.
[8]Tolonate ® HDT LV 100% isocyanate trimer of hexamethylene diisocyanate from Rhodia, Inc, Cranbury, New Jersey.

For the clearcoat above, the constituents of Part 1 were charged into a mixing vessel in the order shown above and mixed then Part 2 was premixed and charged into the mixing vessel and thoroughly mixed with Part 1 to form clearcoat Examples 2. The resulting clear coating compositions had a solid contents of 85-87% and VOC of 0.14-0.64 kg/L (1.16-1.33 lbs/gal).

After the clearcoat was prepared, a phosphatized steel panel was coated with a primer of a Cormax® 6 electrodeposited primer (from DuPont Company) baked at 182° C. for 17 min., a waterborne primer surfacer baked at 163° C. for 30 min, and a waterborne black basecoat prebaked at 83° C. for 5 min to a dry thickness of 15.2 micrometer (0.6 mil). The panel was then topcoated with the clear coating composition of Example 14 and baked at 140° C. for 30 min to a dry film thickness of 51 micrometer (2 mil).

The resulting clearcoat met automotive topcoat standards and exhibited good scratch and mar resistance, excellent primerless adhesion to windshield sealants, and excellent appearance.

Various other modifications, alterations, additions or substitutions of the methods and compositions of this invention will be apparent to those skilled in the art without departing from the spirit and scope of this invention. This invention is not limited by the illustrative embodiments set forth herein, but rather is defined by the following claims.

The invention claimed is:

1. A reactive organosilicon compound comprising the reaction product of: a carboxylic acid of the formula

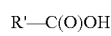

with an epoxy-functional silane of the formula

the reaction product having a number average molecular weight more than 200 and less than about 5000;
wherein:
R' is selected from the group consisting of
a) $C_3$ to $C_{20}$ cycloaliphatic optionally substituted with at least one member selected from the group consisting of O, N, P and S;
b) two or more cycloaliphatic connected to each other through a covalent bond or through an alkylene group of 1 to 5 carbon atoms, or through a heteroatom, or fused together to share to or more carbon atoms, each optionally substituted with at least one member selected from the group consisting of O, N, P and S; and
c) linear polyester, branched polyester, linear and branched polyester, polyacrylate, polyolefin, polyether, polycarbonate, polyurethane, or polyamide;
X is independently selected from the group consisting of alkoxy containing 1 to 20 carbon atoms, carboxyloxy containing 1 to 20 carbon atoms, phenoxy, halogen, amine, amide, urea, imidazole, carbamate, ketoximine, oxazolidinone and a combination thereof;
Y is selected from the group consisting of alkyl of 1 to 12 carbon atoms, aromatic rings or hydrogen;
Z is an epoxy group containing $C_3$ to $C_{20}$ carbon atoms, optionally substituted with O or P; and
n is 1, 2 or 3.

2. The organosilicon compound of claim 1 wherein R' is a cycloaliphatic ring, X is independently selected from a $C_1$ to $C_3$ alkoxy group, Z is an epoxy group containing $C_3$ to $C_{20}$ carbon atoms; and n is 3.

3. The organosilicon compound of claim 1 which is the reaction product of 3-glycidoxypropyltrimethoxysilane with cyclohexanecarboxylic acid.

4. A process for making an organosilicon compound having an average of about one hydroxyl group and about one reactive silyl groups suitable for use in a sprayable coating composition comprising
i) reacting an epoxy-functional silane of the formula shown in claim 1 with a monocarboxylic acid of the formula shown in claim 1, optionally in the presence of a catalyst at a molar ratio of epoxy/acid group in the range of about 0.5 to 5.0 at a temperature in the range of 25-150° C.; and ii) cooling the reaction mixture to room temperature.

5. A moisture cure coating composition wherein the reactive organosilicon compound of claim 1 is used therein as a constituent.

6. A moisture cure adhesive composition wherein the reactive organosilicon compound of claim 1 is used therein as a constituent.

7. A moisture cure sealant composition wherein the reactive organosilicon compound of claim 1 is used therein as a constituent.

* * * * *